United States Patent [19]
Balkovec et al.

[11] Patent Number: 5,948,753
[45] Date of Patent: Sep. 7, 1999

[54] CYCLOHEXAPEPTIDYL PROPANOLAMINE COMPOUNDS

[75] Inventors: James M. Balkovec, North Plainfield; Milton L. Hammond, Somerville; Robert A. Zambias, Springfield, all of N.J.

[73] Assignee: Merck & Co., Inc., Rahway, N.J.

[ * ] Notice: This patent is subject to a terminal disclaimer.

[21] Appl. No.: 08/058,657

[22] Filed: May 4, 1993

[51] Int. Cl.$^6$ .............................. A61K 38/12; C07K 7/54
[52] U.S. Cl. ................................. 514/11; 514/9; 514/2; 530/317; 530/318
[58] Field of Search ..................... 514/11, 9, 2; 530/317, 530/318; 930/270

[56] References Cited

U.S. PATENT DOCUMENTS

| | | | |
|---|---|---|---|
| 4,173,629 | 11/1979 | Dreyfuss et al. | 520/317 |
| 4,287,120 | 9/1981 | Abbott et al. | 530/317 |
| 4,293,485 | 10/1981 | Debono | 530/317 |
| 4,293,489 | 10/1981 | Debono | 530/317 |
| 4,320,053 | 3/1982 | Abbott et al. | 530/317 |
| 4,320,054 | 3/1982 | Abbott et al. | 530/317 |
| 4,931,352 | 6/1990 | Fromtling et al. | 435/71.3 |
| 4,968,608 | 11/1990 | Giacobbe et al. | 435/71 |
| 5,021,341 | 6/1991 | Giacobbe et al. | 435/71.1 |
| 5,021,403 | 6/1991 | Sesin et al. | 514/9 |
| 5,166,135 | 11/1992 | Schmatz | 514/11 |

FOREIGN PATENT DOCUMENTS

| | | |
|---|---|---|
| 851310 | 8/1977 | Belgium . |
| 859067 | 3/1978 | Belgium . |
| 0 447 186 | 3/1991 | European Pat. Off. . |
| 0 459 564 | 5/1991 | European Pat. Off. . |
| 0 451 957 A2 | 12/1991 | European Pat. Off. . |
| 0 486 011A2 | 5/1992 | European Pat. Off. . |
| 500170 | 8/1992 | European Pat. Off. . |
| 561639 | 9/1993 | European Pat. Off. . |

OTHER PUBLICATIONS

Chemical Abstracts, vol. 114, No. 21, pp. 440–441, May 27, 1991.
Kim et al, Antimicrobial Agents and Chemotherapy, vol. 31(2), pp. 197–201 (Feb. 1987).
Bartlett, M.S., et al., Clin. Microbiol. Rev. 4(2):137–149 (Apr. 1991).
Gautier, V., et al., Clin. Exp. Allergy 21:63–66 (1991).
Henson, J.W., et al. Arch. Neurol. 48:406–409 (Apr. 1991).
Varthalitis, I., et al. Cancer 71(s): 481–485 (1993).
Walzer, P.D., et al. Diagn. Microbiol. Infect. Dis. 2: 1–6 (1984).
Walzer, P.D.N. Eng. J. Med. 324(4): 263–265 (1991).
Zambias, et al. J. Med. Chem. 35(15): 2843–2855 (1992).
Jacobs, J.L., et al. N. Eng. J. Med. 324(4): 246–250 (1991).
Pavlica, F. Ann. Paediat. 198 177–184 (1962).
Poplin, E.A., et al. Cancer 68: 193–194 (1991).
Sepkowitz, K.A., et al. JAMA 267(6): 832–837 (1992).
Schmatz, D.M., et al. Workshop on Pneumocystis, Cryptosporidium and Microsporidia suppl to J. Protozoology 38(6): 151S–153S (Nov.–Dec. 1991).
Schmatz, D.M., et al. Antimicrobial Agents and Chemo. 36(9): 1964–1970 (1992).

*Primary Examiner*—Ponnathapura Achutamurthy
*Assistant Examiner*—T. D. Wessendorf
*Attorney, Agent, or Firm*—Elliot Korsen; Mark R. Daniel

[57] ABSTRACT

Certain propanolamine compounds are described which have a cyclohexapeptidyl nucleus and which possess antibiotic activity with physical properties suitable for direct use in therapeutic compositions. A process for their preparation is also described.

7 Claims, No Drawings

CYCLOHEXAPEPTIDYL PROPANOLAMINE COMPOUNDS

The present invention is directed to certain cyclohexapeptidyl propanolamine compounds and to a process for their preparation.

The cyclohexapeptidyl propanolamine compounds of the present invention, Compound A (SEQ ID NOS 1–13 and 40, 41) may be represented by (A)

[Chemical structure of cyclohexapeptide with substituents $R_1$, $R_2$, $R_3$, $R_4$, $R_5$, $R_6$, $R^I$, $R^{II}$, $R^{III}$]

or its acid addition salt.

In the foregoing and succeeding formulas, $R_1$ is H or OH $R_2$ is H or OH $R_3$ is H, OH or OR where R is $C_1$–$C_4$ alkyl or benzyl $R_4$ is H or OH $R_5$ is H, OH or $CH_3$ $R_6$ is H or $CH_3$ $R^I$ is

[Chemical structure: biphenyl group with $OR^a$ substituent and subscript p]

wherein $R^a$ is $c_1$–$C_{10}$ alkyl; or $(CH_2)_q NR^b R^c$ wherein $R^b$ and $R^c$ are independently H, $C_1$–$C_{10}$ alkyl or $R^b$ and $R^c$ taken together are

[Structures: piperidinyl-$R^d$ or piperazinyl-$R^d$]

wherein $R^d$ is $C_1$–$C_{16}$ alkyl, phenyl or benzyl;

$R^{II}$ is H, $C_1$–$C_4$ alkyl or benzyl, $R^{III}$ is H, $C_1$–$C_4$ alkyl or benzyl or $R^{II}$ and $R^{III}$ together is —$(CH_2)_4$— or —$(CH_2)_5$—;

p is an integer of from 1 to 2 inclusive; and q is an integer of from 2 to 4, inclusive.

Hereinafter, when the expression "cyclohexapeptidyl propanolamine compound" or "Compound A" is employed, it is intended to embrace the propanolamine of formula (A) and its acid addition salt.

Where the expression "alkyl", "alkenyl" or "alkoxy" is employed, it is intended to include branched as well as straight chain radicals. It is also intended to include an alkyl chain having a cycloalkyl substituent.

Pharmaceutically acceptable salts suitable as acid addition salts as well as salts providing the anion of the quaternary salt are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in Journal of Pharmaceutical Science, 66, 2 (1977).

Representative nuclei for the propanolamine compounds, Compound A, and the sequence ID for these compounds may be seen in the following table. Since the amino acid nuclei would be the same irrespective of substituents $R^I$, $R^{II}$ or $R^{III}$, the sequence identification number is assigned for the nuclear variations so that the amines and amine salts have the same sequence ID's, as well as compounds having a different lipophilic side chain.

| AMINE COMPOUND | $R_1$ | $R_2$ | $R_3$ | $R_4$ | $R_5$ | $R_6$ | SEQ. ID |
|---|---|---|---|---|---|---|---|
| A-1 | OH | OH | OH | OH | H | $CH_3$ | 1 |
| A-2 | OH | OH | OH | OH | $CH_3$ | $CH_3$ | 2 |
| A-3 | H | OH | OH | OH | $CH_3$ | H | 3 |
| A-4 | OH | H | OH | OH | $CH_3$ | $CH_3$ | 4 |
| A-5 | H | H | OH | H | $CH_3$ | $CH_3$ | 5 |
| A-6 | H | H | H | H | $CH_3$ | $CH_3$ | 6 |
| A-7 | OH | OH | H | H | $CH_3$ | $CH_3$ | 7 |
| A-8 | OH | OH | H | H | H | $CH_3$ | 8 |
| A-9 | OH | OH | OH | OH | OH | $CH_3$ | 9 |
| A-10 | H | OH | OH | OH | H | H | 10 |
| A-11 | H | OH | $OCH_3$ | OH | $CH_3$ | H | 11 |
| A-12 | H | OH | H | OH | H | $CH_3$ | 12 |
| A-13 | OH | OH | H | OH | H | $CH_3$ | 13 |
| A-14 | H | OH | OH | OH | H | $CH_3$ | 40 |
| A-15 | OH | OH | $OCH_3$ | OH | H | $CH_3$ | 41 |

When the compounds are free amines, they are soluble in lower alcohols and polar aprotic solvents such as dimethylformamide (DMF) and pyridine. They are insoluble in solvents such as ether and acetonitrile. The compounds in which $R_3$ is OH may be slowly degraded in aqueous media so they are preferably utilized as acid addition salts.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis* and Aspergillus species such as *A. fumigats, A. flavus, A. niger.* They are also useful for the treatment and/or prevention of *Pneumocystis carinii* pneumonia to which immune compromised patients are especially susceptible as hereinafter described.

The previously noted solubility properties are advantageous for utilization in therapeutic applications, especially in injectible compositions.

The compounds of the present invention may be prepared from a nitrile which in turn is obtained from a derivative of a natural product as hereinafter described.

The nitrites may be represented by compounds of formula (F) (Seq. ID Nos. 14–26 and 42) and the starting materials may be represented by compound formula (E) (Seq. ID Nos. 27–39) as seen in the following diagram:

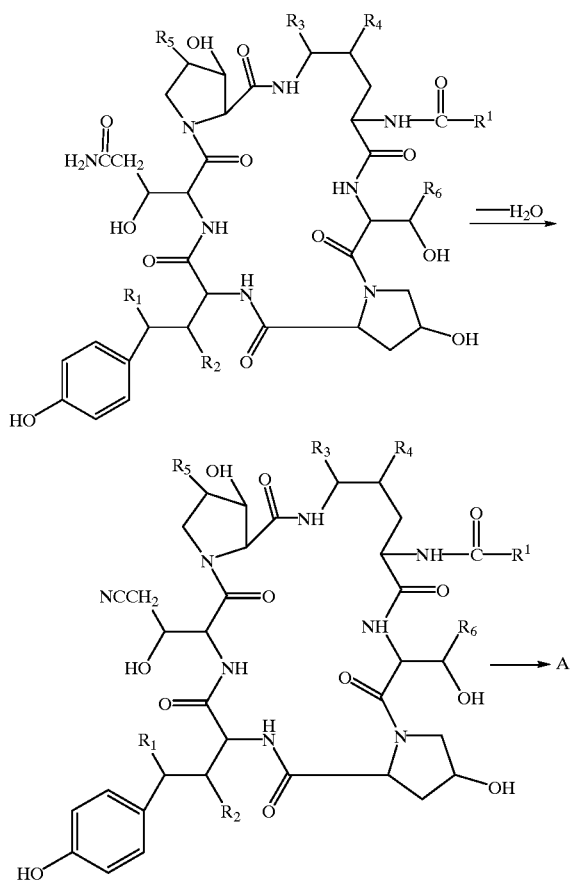

| NITRILE COMPOUND | R₁ | R₂ | R₃ | R₄ | R₅ | R₆ | SEQ. ID |
|---|---|---|---|---|---|---|---|
| F-1 | OH | OH | OH | OH | H | CH₃ | 14 |
| F-2 | OH | OH | OH | OH | CH₃ | CH₃ | 15 |
| F-3 | H | OH | OH | OH | CH₃ | H | 16 |
| F-4 | OH | H | OH | OH | CH₃ | CH₃ | 17 |
| F-5 | H | H | OH | H | CH₃ | CH₃ | 18 |
| F-6 | H | H | H | H | CH₃ | CH₃ | 19 |
| F-7 | OH | OH | H | H | CH₃ | CH₃ | 20 |
| F-8 | OH | OH | H | H | H | CH₃ | 21 |
| F-9 | OH | OH | OH | OH | OH | CH₃ | 22 |
| F-10 | H | OH | OH | OH | H | H | 23 |
| F-11 | H | OH | OCH₃ | OH | CH₃ | H | 24 |
| F-12 | H | OH | H | OH | H | CH₃ | 25 |
| F-13 | OH | OH | H | O | H | CH₃ | 26 |
| F-14 | H | OH | OH | OH | H | CH₃ | 42 |

The sequence identification numbers for the starting materials, Compound E (Seq. ID Nos. 27–39), which correspond to the nitriles and ultimately the amines are seen below. The starting material for F-14 and A-14 is E-1 which is taken through an additional step as subsequently described. The starting material for A-15 also may be E-1; it is etherified E-1.

| STARTING MATERIAL | R₁ | R₂ | R₃ | R₄ | R₅ | R₆ | SEQ. ID |
|---|---|---|---|---|---|---|---|
| E-1 | OH | OH | OH | OH | H | CH₃ | 27 |
| E-2 | OH | OH | OH | OH | CH₃ | CH₃ | 28 |
| E-3 | H | OH | OH | OH | CH₃ | H | 29 |
| E-4 | OH | H | OH | OH | CH₃ | CH₃ | 30 |
| E-5 | H | H | OH | H | CH₃ | CH₃ | 31 |
| E-6 | H | H | H | H | CH₃ | CH₃ | 32 |
| E-7 | OH | OH | H | H | CH₃ | CH₃ | 33 |
| E-8 | OH | OH | H | H | H | CH₃ | 34 |
| E-9 | OH | OH | OH | OH | OH | CH₃ | 35 |
| E-10 | H | OH | OH | OH | H | H | 36 |
| E-11 | H | OH | OCH₃ | OH | CH₃ | H | 37 |
| E-12 | H | OH | H | OH | H | CH₃ | 38 |
| E-13 | OH | OH | H | OH | H | CH₃ | 39 |

In the preparation of Compound A (Seq. ID Nos. 1–13) the carboxamide group of Compound E is dehydrated to the nitrile Compound F. When this method is employed the reaction is preferably carried out under nitrogen with cyanuric chloride in a solvent. It may be carried out in the presence of molecular sieves but if carried out in the absence of sieves, reaction time is critical, and usually order of addition becomes important. In the absence of sieves, or without careful control of reaction time, degradation may occur even when the $R_3$ hydroxyl is protected with an ether group.

Suitable reagents which may be employed in place of cyanuric chloride are anhydrides such as acetic anhydride, trifluoroacetic anhydride and phosphorus pentoxide; acid chlorides such as oxalyl chloride, phosphorus oxychloride, thionyl chloride, p-toluenesulfonyl chloride and chlorosulfonyl isocyanate; phosphonium reagents such as phosphorus pentachloride, triphenylphosphine/carbon tetrachloride, triphenylphosphonium ditriflate and triphenylphosphonium dichloride; carbodiimides such as dicyclohexylcarbodiimide; other dehydrating agents such as aluminum chloride, titanium tetrachloride, ethyl(carboxysulfamoyl) triethylammonium hydroxide inner salt.

Suitable solvents include dimethylformamide or weakly basic solvents such as pyridine, collidine and the like.

Molecular sieves may be in the size range 3A to 5A.

The relative amounts of Compound E (Seq. ID Nos. 27–39) and reagents vary, but in general the dehydrating agent is used in excess. From about 1.5 to 15 equivalents of the dehydrating agent are employed. The molecular sieves are used in amounts of 1 to 10 equivalents.

In carrying out the reaction using sieves, a suspension of molecular sieves in a rigorously dried solvent is first prepared, and while stirring under an atmosphere of nitrogen, there is added, cyanuric chloride or other dehydrating agent and thoroughly mixed. To the resulting mixture while stirring under an atmosphere of nitrogen is added the starting material, Compound E and the stirring continued for about 12 to 24 hours or until HPLC analysis of the reaction mixture indicates substantial completion of the reaction with the formation of the nitrile. The sieves are removed by filtration, preferably on a sintered glass funnel, and the filtrate concentrated and purified by preparative HPLC (such as C18 "ZORBAX", DuPont). The mobile phase used in the purification are varying ratios of a water/acetonitrile composition and an acetonitrile/water composition each containing trifluoroacetic acid (TFA) or acetic acid. These compositions are referred to as A and B. Composition A is 95/5 water/acetonitrile containing 0.1% TFA or acetic acid. Composition B is 95/5 acetonitrile/water containing 0.1% TFA or acetic acid. The exact mobile phase used for HPLC assays and the mobile phase used in preparative HPLCs may differ not only from each other but also from compound to compound but can be determined by the skilled artisan without difficulty.

In carrying out the reaction in the absence of sieves, solid cyanuric chloride is added in a single portion to a solution of Compound E in an aprotic solvent and stirred rapidly for a short time and the reaction mixture then quenched by adding aqueous sodium acetate directly to the reaction mixture. The volatiles are then removed in vacuo to obtain a solid residue which may be purified as above described.

The reduction of the nitrile to the amine may be carried out employing either chemical or catalytic reduction. Sodium borohydride with cobaltous chloride in alcoholic solvent has been found to be particularly useful. When this combination of reagents is used, from about 5 to 50 molar equivalents of sodium borohydride and from 2 to 10 molar equivalents of cobaltous chloride are used for each molar amount of the nitrile.

Other hydride reducing agents such as sodium borohydride, aluminum hydride, diborane, diisobutyl aluminum hydride and the like also may be used. Frequently these reducing agents are used in combination with a Lewis acid such as cobaltous chloride or aluminum chloride as in the present combination of sodium borohydride and cobaltous chloride.

Catalytic hydrogenation also may be carried out over a variety of catalysts including palladium on carbon, platinum oxide, or rhodium on alumina.

Typical solvents depending on the reagent include alcohols, especially methanol and ethanol, dimethylformamide, pyridine, tetrahydrofuran or other ethers.

When the reduction of the nitrile to the amine is carried out using the preferred chemical procedure, the reaction may be carried out by adding the chemical reducing agent to the nitrile in an alcoholic solution under an atmosphere of nitrogen, and stirring until HPLC analysis using detection by ultraviolet absorption at 210 nm shows substantial completion of the reaction. When sodium borohydride is used in combination with cobaltous chloride, cobaltous chloride is added while stiring to a solution in methanol or other solvent of the nitrile, prepared as above described, at ambient temperature, followed by portionwise addition of the sodium borohydride which is accompanied by gas evolution. Stirring is continued for from 12 to 24 hours. Then the mixture is diluted with a highly aqueous mobile phase, 70/30 to 50/50 A:B, acidified with acetic acid or hydrochloric acid conveniently as indicated by pH paper, filtered and purified by chromatography. The eluate fractions are lyophilized to obtain the amine as an acetic acid or hydrochloride addition salt.

The N-alkylated or benzylated compounds may be prepared using any suitable known procedure for preparing secondary or tertiary amines. The N-benzyl compound is best prepared by first preparing a Schiff base with benzaldehyde and thereafter reducing with conventional reducing agents such as those previously noted in connection with the reduction of the nitrile although milder reducing agents may be employed.

When the desired alkyl group on the nitrogen is methyl, the carbon may be introduced by formylating, followed by reduction of the hydroxymethyl group with sodium cyanoborohydride or other reducing agent. When the desired alkyl group on the nitrogen is a higher alkyl, a preferred procedure is a reductive alkylation of an N-benzyl derivative with an aldehyde and a reducing agent such as cyanoborohydride, and purifying the product with reverse phase chromatography to obtain a benzyl and a higher alkyl substituted tertiary amine. The benzyl group may be removed by hydrogenation using palladium on carbon or other suitable catalyst.

The compounds in which $R_3$ is an ether group may be prepared by reacting the cyclopeptidyl amine compound as the starting material with excess alcohol in the presence of an acid such as camphorsulfonic acid and thereafter recovering by preparative HPLC using acetonitrile/water as the mobile phase.

The compounds of the present invention may be employed for the control of many fungi, and particularly against Candida species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1% dextrose (YNBD).

In a representative assay, Compound A is solubilized in 100% dimethyl sulfoxide (DMSO) at an initial concentration of 5 mg/ml. Once dissolved, the drug stock is brought to a concentration of 512 mg/L by dilution in water such that the final DMSO concentration is about 10 percent. The solution is then dispensed via a multichannel pipetter into the first column of a 96-well plate (each well containing 0.075 ml of YNBD), resulting in a drug concentration of 256 mg/L. Compounds in the first column are diluted 2-fold across the rows yielding final drug concentrations ranging from 256 mg/L to 0.12 mg/L.

Four-hour broth cultures of organisms to be tested are adjusted using a spectrophotometer at 600 nm to equal a 0.5 McFarland Standard. This suspension is diluted 1:100 in YNBD to yield a cell concentration of $1-5 \times 10^4$ colony forming units (CFU)/ml. Aliquots of the suspension (0.075 ml) are inoculated into each well of the microtiter plate resulting in a final cell inoculum of $5-25 \times 10^3$. CFU/ml and final drug concentrations ranging from 128 mg/L to 0.06 mg/L. Each assay includes one row for drug-free control wells and one row for cell-free control wells.

After 24 hours of incubation, the microtiter plates are shaken gently on a shaker to resuspend the cells. The MIC-2000 inoculator is used to transfer a 1.5 microliter sample from each well of the 96-well microliter plate to a single reservoir inoculum plate containing Sabouraud dextrose agar (SDA). The inoculated SDA plates are incubated for 24 hours at 35° C. However, for *Cryptoccoccus neoformans* strains, SDA plates were inoculated at 48 hours and incubated 48 hours after being spotted on SDA before making miniumum fungicidal concentration (MFC) readings.

The in vivo effectiveness of the compounds may be demonstrated with Compound A.

Growth from an overnight SDA culture of *Candida albicans* MY 1055 is suspended in sterile saline and the cell concentration determined by hemacytometer count and the cell suspension adjusted to $3.75 \times 10^5$ cells/ml. 0.2 milliliter of this suspension is administered I.V. in the tail vein of mice so that the final inoculum was $7.5 \times 10^4$ cells/mouse.

The assay then is carried out by administering aqueous solutions of Compound A at various concentrations intraperitoneally (I.P.), twice daily (b.i.d.) for four consecutive days to 18 to 20 gram female DBA/2 mice, which previously have been infected with *Candida albicans* in the manner described above. Distilled water is administered I.P. to *C. albicans* challenged mice as controls. After seven days, the mice are sacrificed by carbon dioxide gas, paired kidneys are removed aseptically and placed in sterile polyethylene bags containing 5 milliliters of sterile saline. The kidneys are homogenized in the bags, serially diluted in sterile saline and aliquots spread on the surface of SDA plates. The plates are incubated at 35° C. for 48 hours and yeast colonies are enumerated for determination of colony forming units (CFU) per gram of kidney.

The compounds of the present invention are also useful for inhibiting or alleviating *Pneumocystis carinii* infections in immune compromised individuals. The efficacy of the compounds of the present invention for therapeutic or anti-infective purposes may be demonstrated in studies on immunosuppressed rats.

In a representative study, the effectiveness of Compound A is determined. Sprague-Dawley rats (weighing approximately 250 grams) are immunosuppressed with dexamethasone in the drinking water (2.0 mg/L) and maintained on a low protein diet for seven weeks to induce the development of pneumocystis pneumonia from a latent infection. Before drug treatment, two rats are sacrificed to confirm the presence of *Pneumocystis carinii* pneumonia (PCP). Five rats (weighing approximately 150 grams) are injected twice daily for four days subcutaneously (sc) with Compound A in 0.25 ml of vehicle (distilled water). A vehicle control is also carried out. All animals continue to receive dexamethasone in the drinking water and low protein diet during the treatment period. At the completion of the treatment, all animals are sacrificed, the lungs are removed and processed, and the extent of disease determined by microscopic analysis of stained slides.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound A or one of the components. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound A with the components suitable for the medium desired.

Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and for injecton take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed. For treating mycotic infections, oral administration is frequently preferred.

When the compound is to be employed for control of pneumocystis infections it is desirable to directly treat lung and bronchi. For this reason inhalation methods are preferred. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of Compound A in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE I

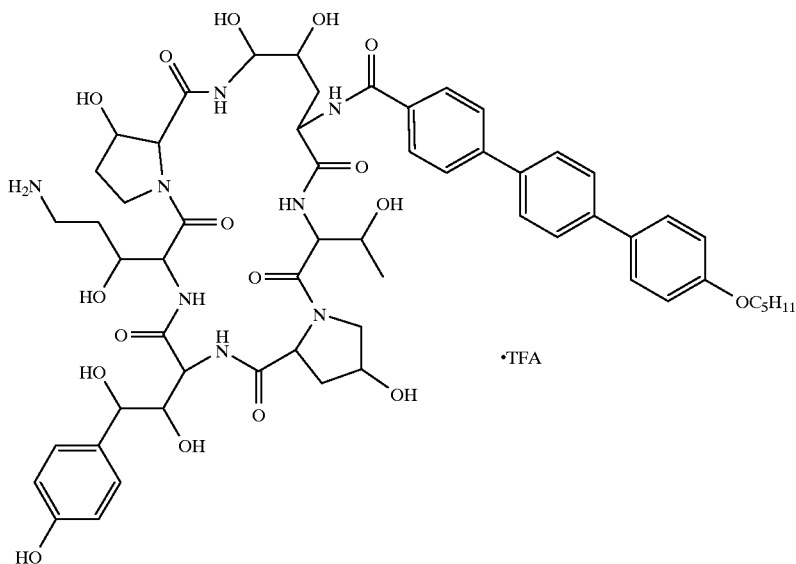

Seq. ID No. 1

A. Preparation of Intermediate Nitrile Compound

A solution of the lipopeptide ($R_1$, $R_2$, $R_3$, $R_4$=OH, $R_5$=H, $R_6$=$CH_3$, $R'$=4"-(n-pentyloxy)-[1,1':4',4"-terphenyl]-4-yl) (1.0 eq) is prepared in sieve-dried DMF and approximately 3 molar equivalents of cyanuric chloride are added in one portion. After 5–6 minutes, the reaction is quenched with 10 molar equivalents of aqueous sodium acetate. The reaction mixture is diluted with 50% aqueous acetonitrile, purified by preparative HPLC (C18 "ZORBAX" DuPont, step gradient starting at 70/30:$H_2O$/$CH_3CN$/0.1% TFA) and the appropriate fractions lyophilized to obtain the desired product as a solid (MW=1151.25).

B. Preparation of the Amine Compound

To a solution of the above nitrile compound (1.0 eq) in methanol is added cobalt (II) chloride (4.0 eq). Next, $NaBH_4$ (20 eq) is added cautiously and in several portions. The black reaction is stirred for several hours at which time sufficient 2N hydrochloric acid is added to effect dissolution of the precipitate. The resulting solution is diluted with water and purified by preparative HPLC (C18 "ZORBAX", step gradient starting at 70/30:$H_2O$/$CH_3CN$/0.1%TFA). The appropriate fractions are combined and lyophilized to obtain the desired water soluble product (MW=1269.32).

EXAMPLE II

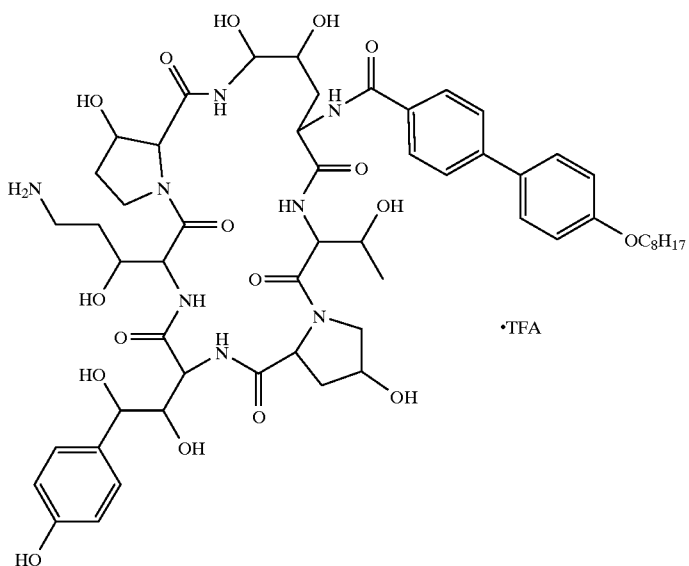

Seq ID No. 1

In a manner similar to steps A and B above in example I but starting with the lipopeptide where $R_1$, $R_2$, $R_3$, $R_4$=OH, $R_5$=H, $R_6$=$CH_3$, $R'$=4'-n-octyloxy-[1,1'-biphenyl]-4-yl), the corresponding amine compound having the above formula may be prepared (MW=1235.29).

EXAMPLE III

To a solution of the triamine compound prepared as described in example III (1 eq) in acetonitrile is added 50 eq of 37% aqueous formaldehyde. Next, sodium cyanoborohydride (8 eq) is added and the mixture stirred at room temperature for 10 minutes. The reaction is neutralized with Seq. ID No. 1

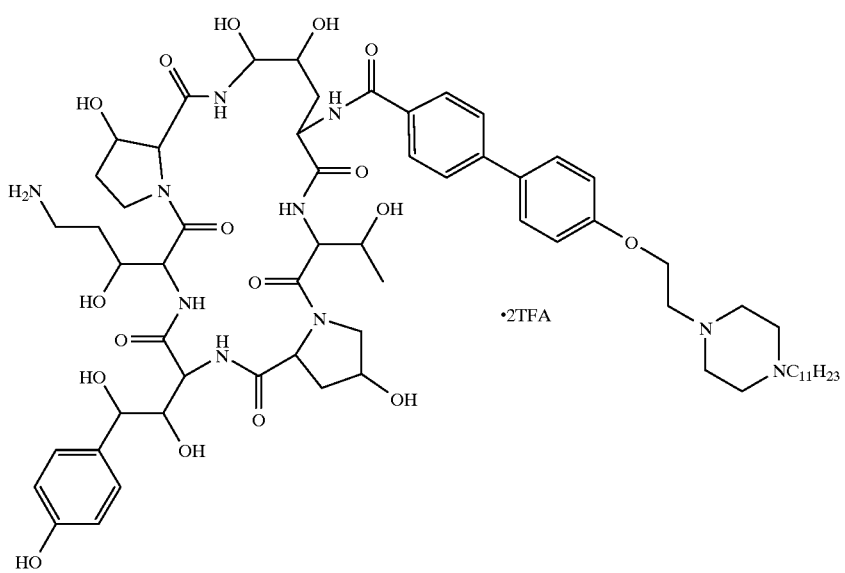

In a manner-similar to steps A and B above in example I but starting with the lipopeptide where $R_1$, $R_2$, $R_3$, $R_4$=OH, $R_5$=H, $R_6$=$CH_3$, $R_f$=4'-(2-[4-undecylpiperazin-1-yl]ethoxy) [1,1'-biphenyl]-4-yl, the corresponding triamine compound having the above formula may be obtained (MW=1503.57).

EXAMPLE IV acetic acid and purified by preparative HPLC (C18 "ZORBAX", step gradient starting at 70/30:$H_2O$/$CH_3CN$/ 0.1%TFA). The appropriate fractions are combined and lyophilized to obtain the desired water soluble product having the above formula (MW=1531.62).

Seq ID No. 1

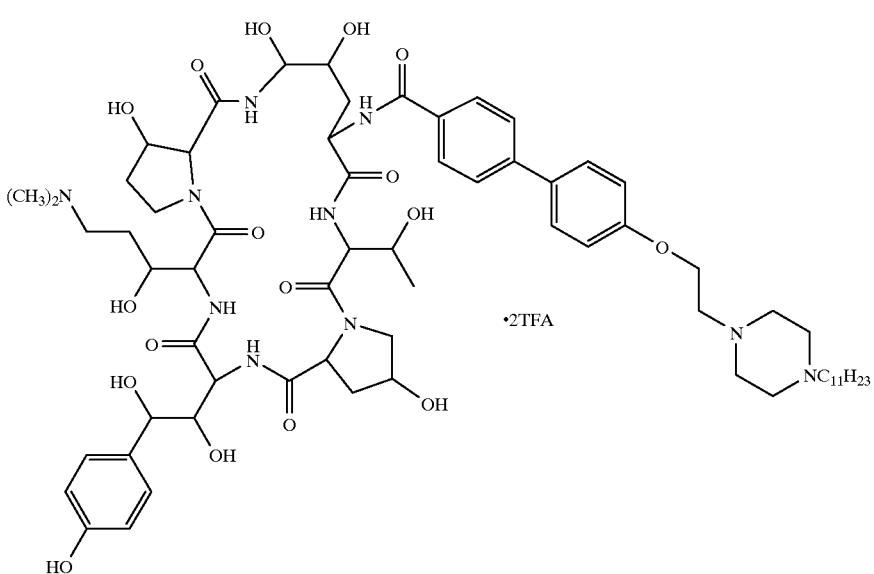

EXAMPLE V

Seq. ID No. 1

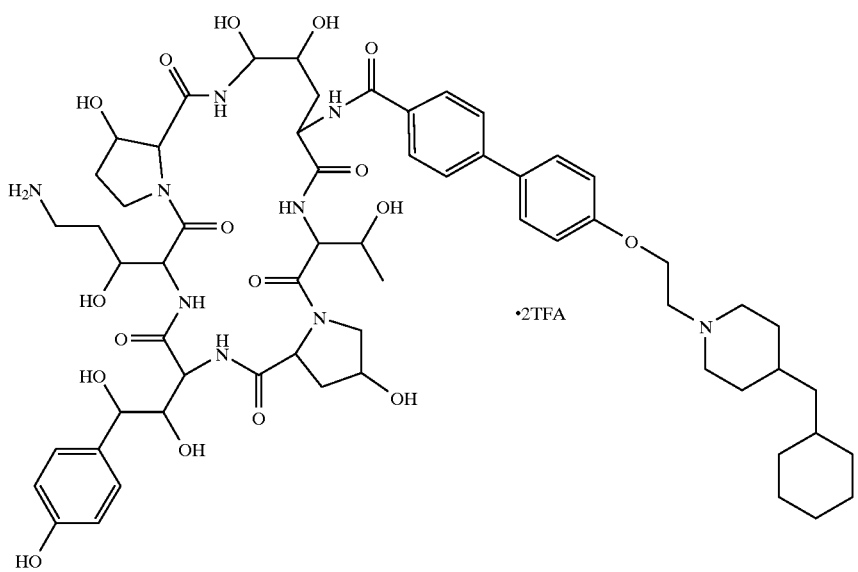

In a manner similar to steps A and B above in Example I but starting with the lipopeptide ($R_1$, $R_2$, $R_3$, $R_4$=OH, $R_5$=H, $R_6$=$CH_3$, $R^I$=4'-(2-[4-cyclohexylmethylpiperidine-1-yl] ethoxy-[1,1'-biphenyl]-4-yl), the corresponding bisamine compound having the above formula may be prepared (MW=1444.46).

EXAMPLE VI

Seq. ID No. 1

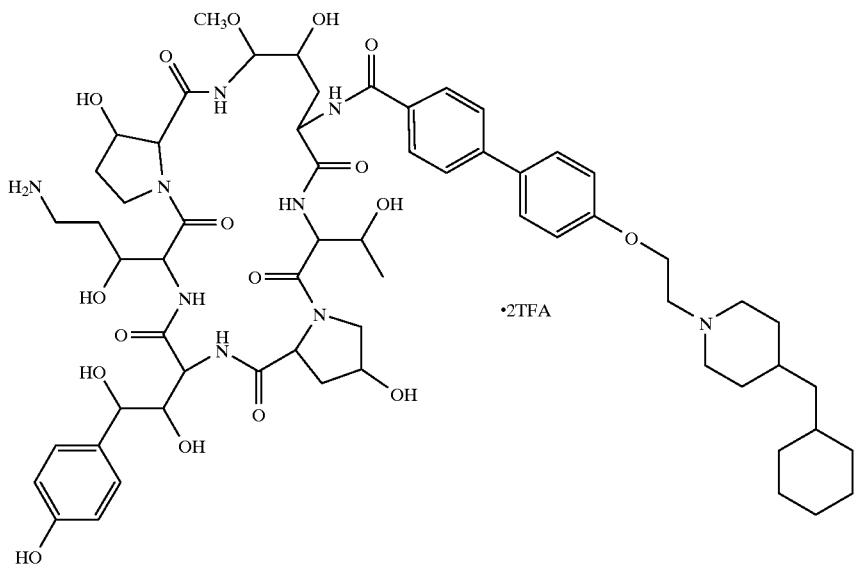

The diamine compound (trifluoroacetic acid salt) from Example V (1 eq) above is dissolved in anhydrous methanol. A catalytic amount of camphorsulfonic acid is added and the mixture is stirred at room temperature for several hours. The reaction is quenched with aqueous sodium bicarbonate and concentrated in vacuo. The residue is dissolved in water and purified by preparative HPLC (C18 "ZORBAX", step gradient starting at 70/30:$H_2O$/$CH_3CN$/0.1% TFA). The appropriate fractions are combined and lyophilized to obtain the desired water soluble methyl ether product having the above formula (MW=1458.48).

EXAMPLE VII

In operations carried out in a manner similar to that described in the foregoing example, a solution of the appropriate lipopeptide is caused to react with cyanuric chloride to obtain a nitrile, and the latter reduced with cobaltous chloride and sodium borohydride to obtain the following compounds where $R_1$, $R_2$ and $R_4$=OH and $R_6$=$CH_3$, and the other groups are as set forth in the following table.

TABLE 1

| EX. | $R_3$ | $R_5$ | $R^{II}$ | $R^{III}$ | $R^I$ | SEQ ID NO |
|---|---|---|---|---|---|---|
| VIIA | OH | H | $CH_3$ | H | p-$(\phi)_3$-$OC_5H_{11}$ | 1 |
| VIIB | OH | $CH_3$ | H | H | p-$(\phi)_3$-$OC_5H_{11}$ | 2 |
| VIIC | OH | OH | H | H | p-$(\phi)_3$-$OC_5H_{11}$ | 9 |
| VIID | $OCH_3$ | H | $CH_2\phi$ | H | p-$(\phi)_2$-$OC_8H_{17}$ | 41 |
| VIIE | $OCH_3$ | H | $C_2H_5$ | $C_2H_5$ | p-$(\phi)_2$-$OC_8H_{17}$ | 41 |
| VIIF | H | H | —$(CH_2)_4$— | | p-$(\phi)_2$-$OC_8H_{17}$ | 13 | p-$(\phi)_3$-$OCH_5H_{11}$ stands for

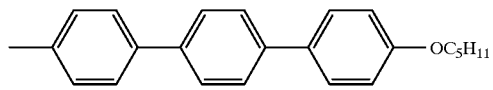

EXAMPLE VIII

In operations carried out in a manner simular to that described in the foregoing examples, the following compounds are prepared where $R_1$, $R^{II}$ and $R^{III}$ are H, and $R_2$ and $R_4$ are OH and the other groups are as set forth in the following table:

TABLE 2

| EX. | $R_3$ | $R_5$ | $R_6$ | $R^I$ | SEQ ID NO |
|---|---|---|---|---|---|
| VIIIA | OH | $CH_3$ | H | 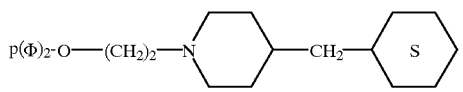 | 3 |
| VIIIB | OH | H | H | 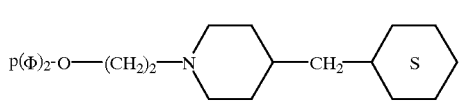 | 10 |
| VIIIC | OH | $CH_3$ | H | 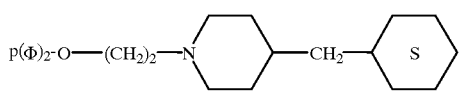 | 11 |
| VIIID | $OCH_3$ | H | $CH_3$ | 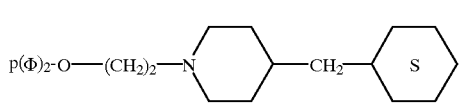 | 40 |
| VIIIE | OH | H | $CH_3$ | 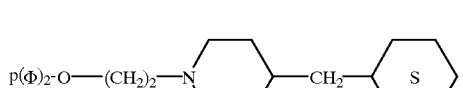 | 12 |

EXAMPLE IX

In still other operations, the following compounds are prepared where $R_6$ is $CH_3$, $R^{II}$ is H and $R^{III}$ is $CH_2C_6H_5$, and the other groups are as set forth in the following table:

TABLE 3

| EX. | $R_1$ | $R_2$ | $R_3$ | $R_4$ | $R_5$ | $R^I$ | SEQ ID NO |
|---|---|---|---|---|---|---|---|
| IXA | OH | H | OH | OH | $CH_3$ | p-$(\phi)$3-$OC_5H_{11}$ | 4 |
| IXB | H | H | OH | H | $CH_3$ | p-$(\phi)$3-$OC_5H_{11}$ | 5 |
| IXC | H | H | H | H | $CH_3$ | p-$(\phi)$3-$OC_5H_{11}$ | 6 |
| IXD | OH | OH | H | H | $CH_3$ | p-$(\phi)$3-$OC_5H_{11}$ | 7 |
| IXE | OH | OH | H | H | H | p-$(\phi)$3-$OC_5H_{11}$ | 8 |

EXAMPLE X 1000 compressed tablets each containing 500 mg of Compound A are prepared from the following formulation:

| Compound | Grams |
|---|---|
| Compound A (of Example I) | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE XI 1000 hard gelatin capsules, each containing 500 mg of Compound A are prepared from the following formulation:

| Compound | Grams |
| --- | --- |
| Compound A (of Example II) | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XVI

An aerosol composition may be prepared having the following formulation:

| | Per Canister |
| --- | --- |
| Compound A (of Example III) | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE XVII 250 milliliters of an injectible solution may be prepared by conventional procedures having the following formulation:

| Dextrose | 12.5 g |
| --- | --- |
| Water | 250 ml |
| Compound A (of Example IV) | 400 mg |

PREPARATION OF STARTING MATERIALS

The starting materials for the compounds are derivatives of natural products. The various nuclei are obtainable by cultivation of the appropriate organism, isolating the natural product which will have the appropriate nucleus with a different lipophilic side chain, then deacylating the lipophilic group, recovering the deacylated cyclopeptide and acylating said cyclopeptide with the appropriate active ester $R_fCOX$ to obtain compound E as hereinafter detailed.

The natural product which differs in the side chain from the starting material are hereafter identified with a prime after the E identification. Thus, the natural product corresponding to the starting material "E-1" is identified below as "E'-1."

E'-1 may be produced by cultivating Zalerion arboricola ATCC 20868 in a nutrient medium enriched in mannitol as the primary source of carbon as described in U.S. Pat. No. 5,021,341, Jun. 4, 1991.

E'-2 may be produced by cultivating Zalerion arboricola ATCC 20868 in nutrient medium as described in U.S. Pat. No. 4,931,352, Jun. 5, 1990 or in nutrient medium enriched in glycerol as described in U.S. Pat. No. 4,968,608, Nov. 6, 1990.

E'-2 nucleus with a different R may be produced by cultivating Acrophialophora limonispora in nutrient medium as described in U.S. Pat. No. 4,173,629.

E'-3, E'-10 and E'-11 may be produced by cultivating Cryptosporiopsis ATCC 20594 in nutrient medium as described by Pache et al in 13th ICC (1983), PS 4.8/3, Part 115, Abstract No. 10 and PCT WO 82/00587.

E'-4, E'-5 and E'-6 may be produced by cultivating Zalerion arboricola ATCC 20868 in nutrient medium as described EPA 0405998, Jan. 1, 1991.

E'-7 may be produced by cultivating Zalerion arboricola ATCC 20958 in nutrient medium as described in U.S. Pat. No. 5,021,403 Jun. 4, 1991.

E'-8 may be produced by cultivating Zalerion arboricola ATCC 20958 in nutrient medium as described in U.S. Pat. No. 5,049,546, Sep. 17, 1991.

E'-9 may be produced by cultivating Zalerion arboricola ATCC 74030 in nutrient medium as described in EPA 0494515, Jul. 15, 1992.

Starting materials which are cyclohexapeptides in which the nucleus of the foregoing has been modified to produce novel hexapeptides in which $R_3$ or both $R_3$ and $R_1$ are hydrogen instead of hydroxyl may be obtained by intimately mixing a compound in which $R_3$ is hydroxyl and $R_1$ may be hydroxyl with a reducing agent such as sodium cyanoborohydride in the presence of a strong acid such as trifluoroacetic acid and the mixture stirred until the reaction is complete. The volatiles are then removed under reduced pressure and the residue purified by reverse phase chromatography employing water/acetonitrile to obtain a purified product. When $R_1$ is OH and it is desired to reduce only $R_3$, essentially the same procedure is used except that the reactant lipopeptide is first dissolved in glacial acetic acid and the reaction carried out in a similar manner as more fully described in U.S. Pat. No. 5,519,059, Oct. 27, 1992. A compound in which $R_1$ and $R_3$ are H, and $R_2$ and $R_4$ are OH, $R_5$ is H and $R_6$ is $CH_3$ may be identified as E-12 and a compound in which $R_3$ is H and $R_1$, $R_2$ and $R_4$ are OH, $R_5$ is H and $R_6$ is $CH_3$ may be identified as E-13.

When $R_1$ is H, $R_2$, $R_3$ and $R_4$ are OH, $R_5$ is H or $CH_3$ and $R_6$ is $CH_3$, the starting material may be made using another starting material, in which $R_1$, $R_2$, $R_3$ and $R_4$ are OH, $R_5$ is H and $R_6$ is $CH_3$ and reducing $R_1$ by methods known to the skilled in the art. Conveniently this may be carried out by adding trifluoroacetic acid to the material and triacetoxyborohydride and mixing together to obtain a product and thereafter purifying the product by conventional methods such as by HPLC.

When $R_1$, $R_2$ and $R_4$ are OH, $R_3$ is $CH_3O$, $R_5$ is H or $CH_3$ and $R_6$ is H or $CH_3$, E'-1 or E'-2 may be first methylated using conventional procedures, or methylation at $R_3$ may be carried out as the last step as in Example VI.

Starting materials E in which $R'$ is as defined are obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experentia 34, 1670 (1978) or U.S. Pat. No. 4,293,482, and thereafter recovering the deacylated cyclopeptide and acylating the deacylated cyclopeptide by mixing together with an appropriate active ester $R'COX$ to obtain Compound E with the desired acyl group as also described in U.S. Pat. Nos. 4,287,120 and 4,293,489.

The active ester $R'COX$ for the side chain $R'$ may be prepared by methods known to the skilled chemist as illustrated in the following examples. Although any active ester is appropriate, the compounds are illustrated with pentafluorophenyl ester.

PREPARATION OF ALKOXYTERPHENYL SIDE CHAINS

The terphenylcarboxylic acid esters may be prepared through the following sequence of reactions, illustrated with a specific example as follows:

A. Preparation of pentyloxyphenyl—substituted—terphenylcarboxylic acid:

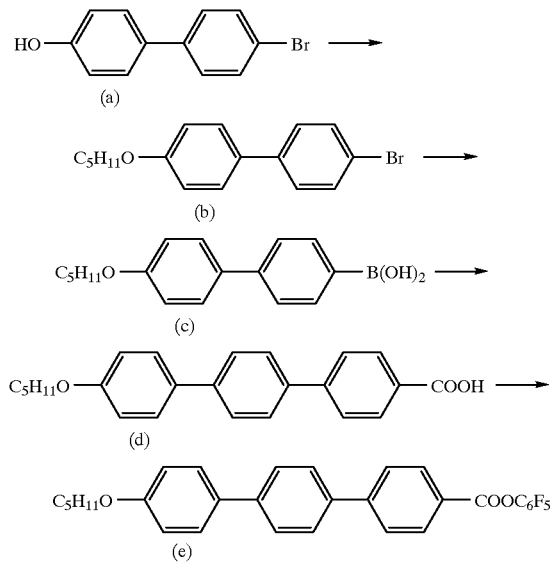

Part A

4-(4-n-Pentyloxyphenyl) bromobenzene

To a stirred solution of 25.5 g of 4-(4-bromophenyl) phenol. (Compound (a)) in 400 mL of dimethylsulfoxide was added 40.9 mL of 2.5 N NaOH, followed by 12.7 mL of n-pentyl bromide, and the resulting mixture heated at 70° C. for 18 hours to obtain in the mixture, compound (b). The mixture was partitioned between 1000 mL of ethyl acetate and 500 mL water and from the organic phase after washing with water and brine, and drying was obtained 30.9 grams of Compound (b) as a white solid.

$^1$H NMR (400 MHz, DMSO-d$_6$) δ 0.93 (t, J=7.2 Hz, 3H), 1.41 (m, 4H), 1.79 (m, 2H), 3.97 (t, J=6.6 Hz, 2H) 6.94 (d, J=8.8 Hz, 2H), 7.39 (d, J=8.6 Hz, 2H), 7.45 (d, J=8.8 Hz, 2H), 7.51 (d, J=8.6 Hz, 2H).

Part B

4-(4-n-Pentyloxyphenyl)phenylboronic acid

To a stirred suspension of 1.0 grams of Compound (b) in 20 mL anhydrous tetrahydrofuran at −78° C. under a nitrogen atmosphere was added 1.32 mL of n-butyl lithium 2.5 M in hexanes. After 15 minutes 0.760 mL of tri-isopropyl borate was added and the stirring continued at −78° C. for 15 minutes and then at 25° C. for 40 minutes. The mixture is acidified and partitioned between ether and water to obtain the boronic acid compound (c) in the reaction mixture. The compound was recovered by washing with water and brine and drying to obtain 750 mg of 4-(4-n-pentyloxyphenyl) phenylboronic acid as white solid with following $^1$H NMR.

$^1$H NMR (400 MHz, DMSO-d$_6$) δ 0.89 (t, J=7.2 Hz, 3H), 1.38 (m, 4H), 1.72 (m, 2H), 3.99 (t, J=6.5 Hz, 2H) 6.99 (d, J=8.8 Hz, 2H), 7.57 (d, J=8.2 Hz, 2H), 7.60 (d, J=8.8 Hz, 2H), 7.83 (d, J=8.2 Hz, 2H)

Part C

Pentafluorophenyl 4"-(n-pentyloxy)-[1,1':4',4"-terphenyl]-4-carboxylate

To a stirred mixture of 1.0 g of the boronic acid and 0.0874 mL of 4-iodobenzoic acid in 11 mL ethanol and 30 mL toluene was added 5.3 mL of a 2 M aqueous solution of sodium carbonate followed by 204 mg tetrakis (triphenylphosphine)palladium and the reaction mixture heated under reflux (100° C.) for 18 hours. Thereafter, the mixture was cooled, acified and partitioned between ethyl acetate and water. The organic phase was washed with water and brine and dried, then filtered through a bed of celite to obtain after removal of solvent and purification with flash silica gel chromatography to obtain 4"-(n-pentyloxy)-[1,':4',4"-terphenyl]-4-carboxylic acid.

$^1$H NMR (400 MHz, DMSO-d$_6$) δ 0.89 (t, 3H), 1.37 (m, 4H), 1.72 (m, 2H), 3.98 (t, 2H) 7.01 (d, 2H).

To a mixture of 4"-(n-pentyloxy)-[1,1':4',4"-terphenyl]-4-carboxylic acid (10.5 mmol) and dicyclohexylcarbodiimide (10.5 mmol) in ethyl acetate at 0° C. is added pentafluorophenol (11.5 mmol). The mixture is stirred at 25° C. for a period of 18 h, producing a precipitate. The mixture is filtered. The filtrate is washed with water and brine and dried with magnesium sulfate. The solvent is removed in vacuo to obtain pentafluorophenyl 4"-(n-pentyloxy)-[1,1':4',4"-terphenyl]-4-carboxylate, C$_{30}$H$_{23}$F$_5$O$_3$, M.W.=526.5.

PREPARATION OF ALKOXY BIPHENYL SIDE CHAINS

The biphenylcarboxylic acid esters may be obtained through the following sequence of reactions illustrated as follows:

A. Preparation of Octyloxybiphenylcarboxylic acid

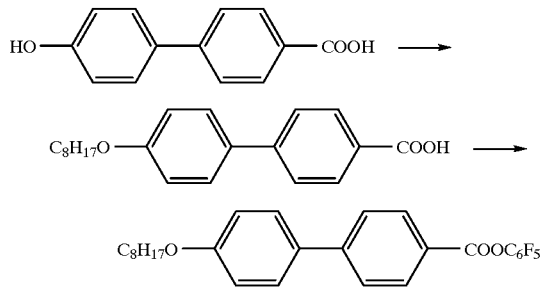

n-Octyl bromide (0.102 mol) is added to a solution of 4-(4-hydroxyphenyl)benzoic acid (0.102 mol) and 2.5 N sodium hydroxide (0.102 mol) and the mixture stirred at 70° C. for a period of 18 hours. The reaction mixture is allowed to cool and then acidified to pH 3 and partitioned between ethyl acetate and water. The organic phase is washed with water and brine and the solvent then removed to obtain the 4'-n-octyloxy-[1,1'-biphenyl]-4-ylcarboxylic acid, C$_{21}$H$_{23}$O$_3$, M.W. 326.4

B. Preparation of pentafluorophenyl Ester

Pentafluorophenol (11.5 mmol) is added at 0° C. to a mixture of 10.5 mmol 4'-n-octyloxy-[1,1'-biphenyl]-4-ylcarboxylic acid and 10.5 mmol of dicyclohexylcarbodiimide in ethyl acetate. The mixture is stirred at 25° C. for a period of 18 hours whereupon a precipitate is formed. The reaction mixture is filtered, the filtrate washed with water and brine and dried, the solvent removed in vacuo to obtain pentafluorophenyl 4'-n-octyloxy[1,1'-biphenyl]-4-ylcarboxylate, C$_{27}$H$_{25}$F$_5$O$_3$, M.W. 492.5.

PREPARATION OF AMINOETHYLOXYBIPHENYL SIDE CHAINS

Preparation of 4'-(2-[4-Cyclohexylmethylpiperidin-1-yl]ethoxy)-[1,1'-biphenyl]-4-ylcarboxylic acid, Pentafluorophenyl Ester

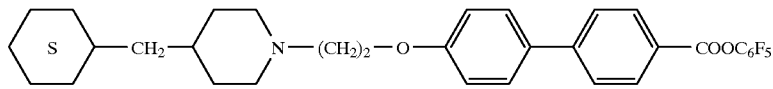

Part A

Preparation of 4-Cyclohexylmethylpiperidine

4-Benzylpiperidine is dissolved in glacial acetic acid containing $PtO_2$ (approximately 50 wt percent). A Paar hydrogenator is used and the reaction vessel is flushed with $H_2$ and pressurized to 3 atm. The mixture is shaken for sufficient time to give reduction of the aromatic ring to the fully saturated product which is determined by the uptake of 3 molar equivalents of $H_2$. The black solid is filtered and the acetic acid removed by evaporation under reduced pressure to obtain the product as an acetate salt.

Part B

Preparation of 1-(2-Hydroxyethyl)-4-cyclohexylmethylpiperidine

The product from Part A (1.0 eq) is dissolved in dichloromethane containing an equimolar amount of diisopropylethyl amine. Ethylene oxide (10 eq) is added and the mixture is stirred until starting material is consumed. The desired product is obtained by removal of the solvent in vacuo followed by purification by column chromatography.

Part C

Preparation of 4'-(2-[4-cyclohexylmethylpiperidine-1-yl/ethoxy)-[1,1'-biphenyl]-4-ylcarboxylic acid 4'-Hydroxy-[1,1'-biphenyl-4-ylcarboxylic acid methyl ester (1.0 eq) is dissolved in dichloromethane and then triphenylphosphine (1.3 eq) and the hydroxyethyl compound (1.0 eq) from Part B are added. Next, diethyl azodicarboxylate (1.3 eq) is added and the mixture is stirred until starting material is consumed. The mixture is diluted with dichloromethane and washed with water. The organic layer is dried with $MgSO_4$ and filtered. The solvent is removed in vacuo and the residue is dissolved in ethanol. An excess of 3N sodium hydroxide is added and the mixture stirred for several hours. The reaction is neutralized with 2N HCl and is extracted with ethyl acetate. The ethyl acetate layer is dried with $MgSO_4$, filtered and the solvent vaporized under reduced pressure. The desired product is obtained in substantially pure form by column chromatography.

Part D

Preparation of the Pentafluorophenyl Ester

The carboxylic acid (1.0 eq) and dicyclohexylcarbodiimide (1.0 eq) are dissolved in ethyl acetate and the solution is cooled to 0° C. Pentafluorophenol (1.05 eq) is added, the ice bath then is removed and the reaction stirred at ambient temperature for 18–24 h. An equal volume of ether is added, the mixture is filtered and the solvent removed in vacuo. The product (MW=587.64) is sufficiently pure to be utilized "as is" for nucleus acylation.

Preparation of 4'-(2-[4-Undecylpiperizin-1-yl]-ethoxy)[1,1'-biphenyl]-4-ylcarboxylic acid, Pentafluorophenyl Ester

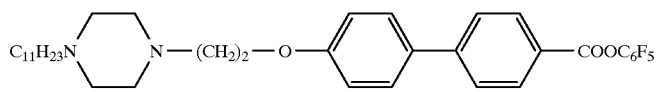

Part A

Preparation of 4-Undecylpiperazine

Excess piperazine (5 eq) and 1-bromoundecane (1.0 eq) are dissolved in dichloromethane and allowed to react overnight. The mixture is extracted with aqueous sodium bicarbonate and the organic layer dried with sodium sulfate. The mixture is filtered, the solvent removed in vacuo and the residue purified by column chromatography.

Part B

Preparation of 1(2-Hydroxyethyl)-4-undecylpiperazine

The substituted piperazine above (1.0 eq) is dissolved in n-propanol and bromoethanol (1.0 eq) is added along with diisopropylethyl amine (1.1 eq). After several hours, the solvent is removed in vacuo and the residue dissolved in dichloromethane. The organic layer is washed with water and then aqueous sodium bicarbonate. The organic layer is dried with $MgSO_4$ and filtered. Removal of the solvent in vacuo is followed by purification by column chromatography.

Part C

Preparation of the Carboxylic Acid

The procedure is essentially the same as describe in Part C above except that the hydroxyethyl piperazine from above is substituted for the hydroxyethyl piperidine.

Part D

Preparation of the Pentafluorophenyl Ester

The procedure is identical to Part D from above except that the piperazine acid yl ethoxy substituted biphenylyl is used. The product (MW=646.75) is sufficiently pure to be utilized "as is" in nucleus acylation.

What is claimed is:

1. A compound of the formula

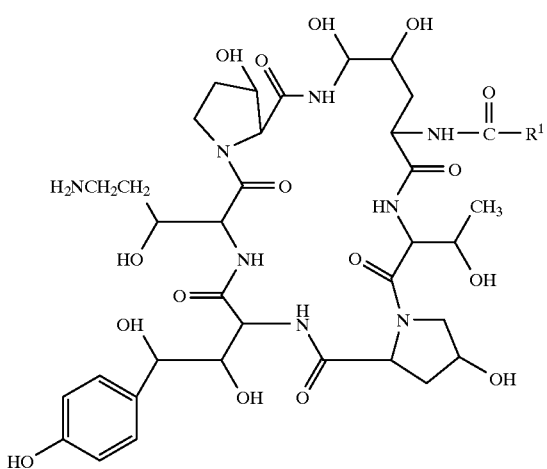

or its pharmaceutically acceptable acid addition salts, wherein $R^I$ is

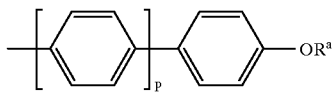

wherein $R^a$ is $C_1$–$C_{10}$ alkyl; or $(CH_2)_q NR^b R^c$ wherein $R^b$ and $R^c$ are independently H, $C_1$–$C_{10}$ alkyl or $R^b$ and $R^c$ taken together are

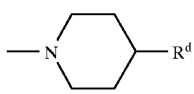

or

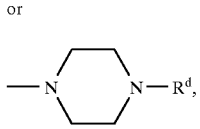

wherein $R^d$ is $C_1$–$C_{16}$ alkyl, phenyl or benzyl;

p is 1 or 2; and q is 2, 3, or 4.

2. A compound according to claim 1 having the formula:

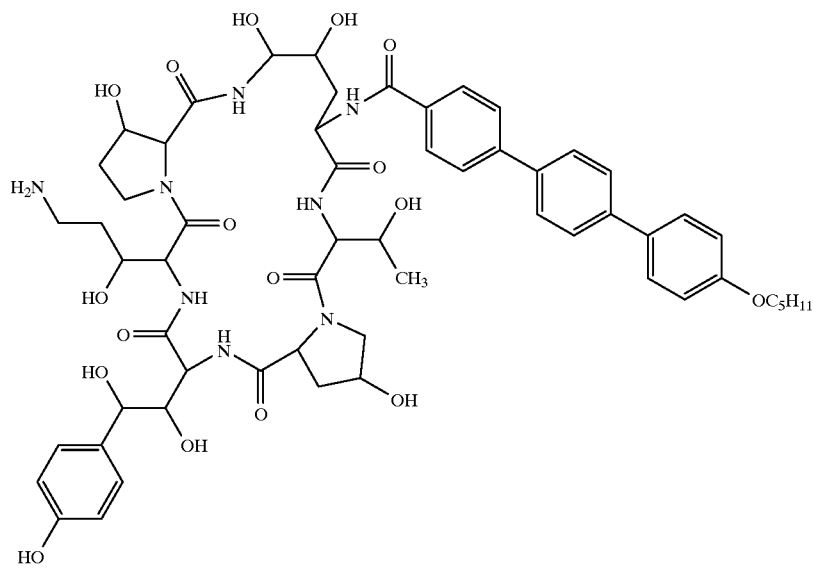

3. A compound according to claim 1 having the formula:
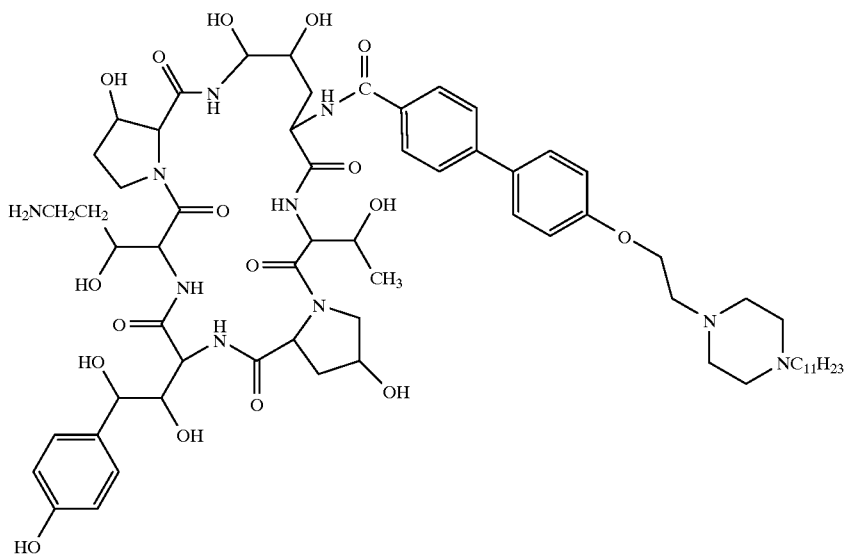
4. A compound according to claim 1 having the formula:
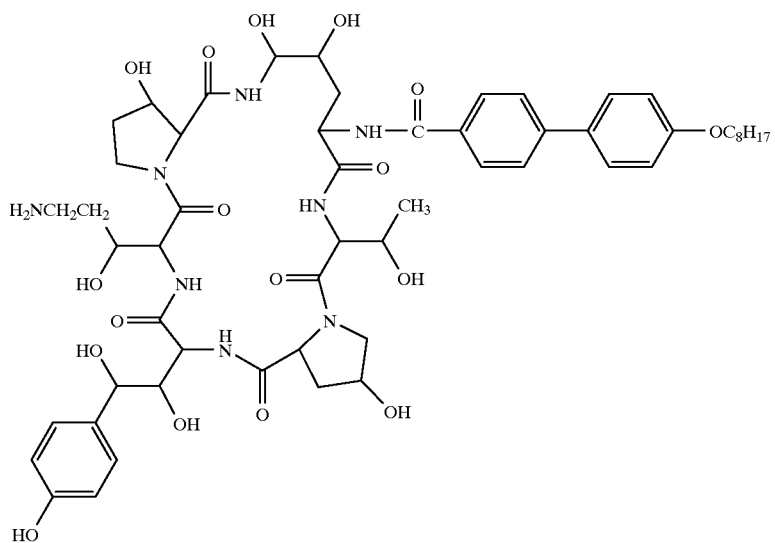

5. A compound according to claim 1 having the formula:
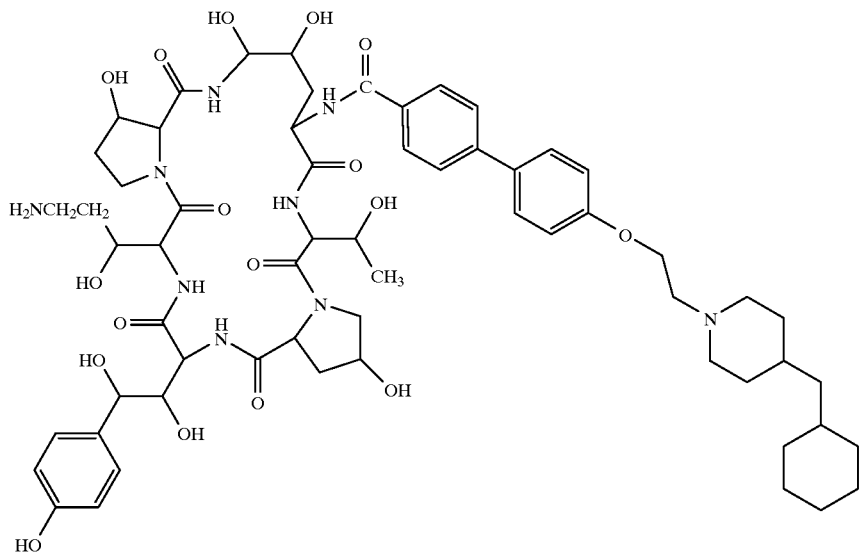
6. An antibiotic composition comprising an antimicrobial amount of a compound of claim 1 in combination with a pharmaceutically acceptable carrier.
7. A composition according to claim 6 in unit dosage form wherein the compound of claim 1 is present in an amount of 100 mg to 200 milligrams.
* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 6
      (B) TYPE: AMINO ACID
      (C) STRANDEDNESS: Not Relevant
      (D) TOPOLOGY: CIRCULAR (ii) MOLECULE TYPE:
      (A) DESCRIPTION: PEPTIDE (xi) SEQUENCE DESCRIPTION: SEQ ID NO: 1:

Xaa Thr Xaa Xaa Xaa Xaa
1           5

(2) INFORMATION FOR SEQ ID NO:2:

(i) SEQUENCE CHARACTERISTICS:
      (A) LENGTH: 6
      (B) TYPE: AMINO ACID
      (C) STRANDEDNESS: Not Relevant
      (D) TOPOLOGY: CIRCULAR (ii) MOLECULE TYPE:
      (A) DESCRIPTION: PEPTIDE (xi) SEQUENCE DESCRIPTION: SEQ ID NO: 2:

Xaa Thr Xaa Xaa Xaa Xaa
1           5

(2) INFORMATION FOR SEQ ID NO:3:

(i) SEQUENCE CHARACTERISTICS:
      (A) LENGTH: 6
      (B) TYPE: AMINO ACID
      (C) STRANDEDNESS: Not Relevant
      (D) TOPOLOGY: CIRCULAR (ii) MOLECULE TYPE:
      (A) DESCRIPTION: PEPTIDE (xi) SEQUENCE DESCRIPTION: SEQ ID NO: 3:

Xaa Ser Xaa Xaa Xaa Xaa
1           5

(2) INFORMATION FOR SEQ ID NO:4:

(i) SEQUENCE CHARACTERISTICS:
      (A) LENGTH: 6
      (B) TYPE: AMINO ACID
      (C) STRANDEDNESS: Not Relevant
      (D) TOPOLOGY: CIRCULAR (ii) MOLECULE TYPE:
      (A) DESCRIPTION: PEPTIDE (xi) SEQUENCE DESCRIPTION: SEQ ID NO: 4:

Xaa Thr Xaa Xaa Xaa Xaa
1           5

(2) INFORMATION FOR SEQ ID NO:5:

(i) SEQUENCE CHARACTERISTICS:
      (A) LENGTH: 6

```
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 5:

Xaa Thr Xaa Xaa Xaa Xaa
1               5

(2) INFORMATION FOR SEQ ID NO:6:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 6:

Xaa Thr Xaa Xaa Xaa Xaa
1               5

(2) INFORMATION FOR SEQ ID NO:7:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 7:

Xaa Thr Xaa Xaa Xaa Xaa
1               5

(2) INFORMATION FOR SEQ ID NO:8:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 8:

Xaa Thr Xaa Xaa Xaa Xaa
1               5

(2) INFORMATION FOR SEQ ID NO:9:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 9:

Xaa Thr Xaa Xaa Xaa Xaa
1               5
```

(2) INFORMATION FOR SEQ ID NO:10:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 10:

Xaa Ser Xaa Xaa Xaa Xaa
1               5

(2) INFORMATION FOR SEQ ID NO:11:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 11:

Xaa Ser Xaa Xaa Xaa Xaa
1               5

(2) INFORMATION FOR SEQ ID NO:12:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 12:

Xaa Thr Xaa Xaa Xaa Xaa
1               5

(2) INFORMATION FOR SEQ ID NO:13:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 13:

Xaa Thr Xaa Xaa Xaa Xaa
1               5

(2) INFORMATION FOR SEQ ID NO:14:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 14:

Xaa Thr Xaa Xaa Xaa Xaa
1               5

(2) INFORMATION FOR SEQ ID NO:15:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 15:

Xaa Thr Xaa Xaa Xaa Xaa
1               5

(2) INFORMATION FOR SEQ ID NO:16:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 16:

Xaa Ser Xaa Xaa Xaa Xaa
1               5

(2) INFORMATION FOR SEQ ID NO:17:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 17:

Xaa Thr Xaa Xaa Xaa Xaa
1               5

(2) INFORMATION FOR SEQ ID NO:18:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 18:

Xaa Thr Xaa Xaa Xaa Xaa
1               5

(2) INFORMATION FOR SEQ ID NO:19:

(i) SEQUENCE CHARACTERISTICS:
          (A) LENGTH: 6
          (B) TYPE: AMINO ACID
          (C) STRANDEDNESS: Not Relevant (D) TOPOLOGY: CIRCULAR (ii) MOLECULE TYPE:
            (A) DESCRIPTION: PEPTIDE (xi) SEQUENCE DESCRIPTION: SEQ ID NO: 19:

Xaa Thr Xaa Xaa Xaa Xaa
1               5

(2) INFORMATION FOR SEQ ID NO:20:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 20:

Xaa Thr Xaa Xaa Xaa Xaa
1               5

(2) INFORMATION FOR SEQ ID NO:21:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 21:

Xaa Thr Xaa Xaa Xaa Xaa
1               5

(2) INFORMATION FOR SEQ ID NO:22:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 22:

Xaa Thr Xaa Xaa Xaa Xaa
1               5

(2) INFORMATION FOR SEQ ID NO:23:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 23:

Xaa Ser Xaa Xaa Xaa Xaa
1               5

(2) INFORMATION FOR SEQ ID NO:24:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 24:

Xaa Ser Xaa Xaa Xaa Xaa
 1               5

(2) INFORMATION FOR SEQ ID NO:25:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 25:

Xaa Thr Xaa Xaa Xaa Xaa
 1               5

(2) INFORMATION FOR SEQ ID NO:26:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 26:

Xaa Thr Xaa Xaa Xaa Xaa
 1               5

(2) INFORMATION FOR SEQ ID NO:27:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 27:

Xaa Thr Xaa Xaa Xaa Xaa
 1               5

(2) INFORMATION FOR SEQ ID NO:28:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 28:

Xaa Thr Xaa Xaa Xaa Xaa
1               5

(2) INFORMATION FOR SEQ ID NO:29:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 29:

Xaa Ser Xaa Xaa Xaa Xaa
1               5

(2) INFORMATION FOR SEQ ID NO:30:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 30:

Xaa Thr Xaa Xaa Xaa Xaa
1               5

(2) INFORMATION FOR SEQ ID NO:31:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 31:

Xaa Thr Xaa Xaa Xaa Xaa
1               5

(2) INFORMATION FOR SEQ ID NO:32:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
          (A) DESCRIPTION: PEPTIDE (xi) SEQUENCE DESCRIPTION: SEQ ID NO: 32:

Xaa Thr Xaa Xaa Xaa Xaa
1               5

(2) INFORMATION FOR SEQ ID NO:33:

(i) SEQUENCE CHARACTERISTICS:
          (A) LENGTH: 6
          (B) TYPE: AMINO ACID
          (C) STRANDEDNESS: Not Relevant
          (D) TOPOLOGY: CIRCULAR (ii) MOLECULE TYPE:
            (A) DESCRIPTION: PEPTIDE (xi) SEQUENCE DESCRIPTION: SEQ ID NO: 33:

Xaa Thr Xaa Xaa Xaa Xaa
1               5

(2) INFORMATION FOR SEQ ID NO:34:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 34:

Xaa Thr Xaa Xaa Xaa Xaa
1               5

(2) INFORMATION FOR SEQ ID NO:35:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 35:

Xaa Thr Xaa Xaa Xaa Xaa
1               5

(2) INFORMATION FOR SEQ ID NO:36:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 36:

Xaa Ser Xaa Xaa Xaa Xaa
1               5

(2) INFORMATION FOR SEQ ID NO:37:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 37:

Xaa Ser Xaa Xaa Xaa Xaa
1               5

(2) INFORMATION FOR SEQ ID NO:38:

(i) SEQUENCE CHARACTERISTICS:

```
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 38:

Xaa Thr Xaa Xaa Xaa Xaa
1               5

(2) INFORMATION FOR SEQ ID NO:39:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 39:

Xaa Thr Xaa Xaa Xaa Xaa
1               5

(2) INFORMATION FOR SEQ ID NO:40:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 40:

Xaa Thr Xaa Xaa Xaa Xaa
1               5

(2) INFORMATION FOR SEQ ID NO:41:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 41:

Xaa Thr Xaa Xaa Xaa Xaa
1               5

(2) INFORMATION FOR SEQ ID NO:42:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE
```

(xi) SEQUENCE DESCRIPTION: SEQ ID NO: 42:

Xaa Thr Xaa Xaa Xaa Xaa
1               5